United States Patent
Narasimhan et al.

(10) Patent No.: US 7,118,897 B2
(45) Date of Patent: Oct. 10, 2006

(54) PROCESS FOR THE EXTRACTION OF POLYHYDROXYALKANOATES FROM BIOMASS

(75) Inventors: Karunakaran Narasimhan, West Chester, OH (US); Isao Noda, Fairfield, OH (US); Michael Matthew Satkowski, Oxford, OH (US); Angella Christine Cearley, Hamilton, OH (US); Michael Steven Gibson, Cincinnati, OH (US); Stanley James Welling, Liberty Township, OH (US)

(73) Assignee: The Procter & Gamble Company

( * ) Notice: Subject to any disclaimer, the term of this patent is extended or adjusted under 35 U.S.C. 154(b) by 0 days.

(21) Appl. No.: 11/225,358

(22) Filed: Sep. 13, 2005

(65) Prior Publication Data
US 2006/0057692 A1 Mar. 16, 2006

Related U.S. Application Data

(60) Provisional application No. 60/610,091, filed on Sep. 15, 2004.

(51) Int. Cl.
*C12P 7/62* (2006.01)
(52) U.S. Cl. ...................................... 435/135
(58) Field of Classification Search ................. 435/135
See application file for complete search history.

(56) References Cited

U.S. PATENT DOCUMENTS

| 4,101,533 | A | | 7/1978 | Lafferty et al. |
| 5,821,299 | A | | 10/1998 | Noda |
| 5,894,062 | A | | 4/1999 | Liddell |
| 5,942,597 | A | * | 8/1999 | Noda et al. .................. 528/361 |
| 6,228,934 | B1 | | 5/2001 | Horowitz et al. |
| 6,329,183 | B1 | * | 12/2001 | Skraly et al. ................ 435/135 |
| 6,340,580 | B1 | * | 1/2002 | Horowitz ..................... 435/135 |
| 6,576,450 | B1 | * | 6/2003 | Skraly et al. ................ 435/135 |
| 2005/0228168 | A1 | * | 10/2005 | Kinoshita et al. ............ 528/495 |
| 2005/0239998 | A1 | * | 10/2005 | Kinoshita et al. ............ 528/272 |

FOREIGN PATENT DOCUMENTS

GB  2 120 671 A  12/1983

OTHER PUBLICATIONS

Braunegg et al, "Polyhydroxyalkanoates, biopolyesters from renewable resources" Journal Biotechnology 65 (1998) 127-161, see p. 144.*
International Search Report dated Jan. 16, 2006, 4 pages. PCT/US05/032873.

* cited by examiner

*Primary Examiner*—Herbert J. Lilling
(74) *Attorney, Agent, or Firm*—Armina E. Matthews; Brahm J. Corstanje; Kim William Zerby

(57) ABSTRACT

The invention relates to processes for extracting polyhydroxyalkanoate from a biomass, comprising admixing the biomass with an organic solvent for from 1 second to 15 minutes at a first temperature of from 5° C. below the melting point of the polyhydroxyalkanoate to 10° C. above the melting point of the polyhydroxyalkanoate and at a pressure of from 1 bar to 10 bar to provide a composition comprising the organic solvent and polyhydroxyalkanoate.

29 Claims, No Drawings

PROCESS FOR THE EXTRACTION OF POLYHYDROXYALKANOATES FROM BIOMASS

CROSS REFERENCE TO RELATED APPLICATIONS

This application claims the benefit of U.S. Provisional Application No. 60/610,091 filed Sep. 15, 2004.

FIELD OF THE INVENTION

This invention relates to processes that are useful for the extraction of polyhydroxyalkanoates from a biomass, such as a plant or a bacterial biomass.

BACKGROUND OF THE INVENTION

Plastics such as polyesters are typically produced from petrochemical sources by well-known synthetic means. These petrochemical-based polymers can take centuries to degrade after disposal. Concern over plastic-waste accumulation in landfills has resulted in a recent movement toward using biodegradable polymers instead.

Bio-based biodegradable polymers, also commonly referred to as "bioplastics," have not enjoyed great success in the marketplace due to their high production cost. However, advances in biotechnology have led to less expensive methods for their production. In one instance, biodegradable aliphatic copolyesters are now often produced by large-scale bacterial fermentation. Collectively termed polyhydroxyalkanoates, also known as "PHAs," these polymers can be synthesized by a plant or bacteria fed with a particular substrate, such as glucose, in a fermentation plant. In many instances, the structural or mechanical properties of PHAs can be customized to fit the specifications of the desired end product. PHAs can biodegrade both aerobically and anaerobically.

PHAs are enormously versatile, and as many as 100 different PHA structures have been identified. PHA structures can vary in two ways. First, PHAs can vary according to the structure of the pendant groups, which are typically attached to a carbon atom having (D)-stereochemistry. The pendant groups form the side chain of hydroxyalkanoic acid not contributing to the PHA carbon backbone. Second, PHAs can vary according to the number and types of their repeat units. For example, PHAs can be homopolymers, copolymers, or terpolymers. These variations in PHA structure can cause variations in their physical characteristics. These physical characteristics make PHAs useful for a number of products that may be commercially valuable.

However, in order to have any type of commercially marketable PHA bioplastic product, there is a need for an efficient process for separating such PHAs from the residual biomass.

Numerous solvent-based and other types of extraction techniques are known in the art for extracting PHAs from a biomass. Solvent-based systems (including those utilizing ketones, toluene, alcohols, alone and in combination with other solvents), mechanical systems, and combinations thereof may be used for extracting PHA.

Typically the solubility of the polymer is not high enough to make it economical. Therefore, there is a need for a more efficient and cost-saving process to load more polymer into the organic solvent for extracting the PHA materials from biomass.

SUMMARY OF THE INVENTION

The present invention relates to processes for extracting polyhydroxyalkanoate from a biomass, comprising admixing the biomass with an organic solvent for from 1 second to 15 minutes at a first temperature of from 5° C. below the melting point of the polyhydroxyalkanoate to 10° C. above the melting point of the polyhydroxyalkanoate and at a pressure of from 1 bar to 10 bar to provide a composition comprising the organic solvent and polyhydroxyalkanoate.

DETAILED DESCRIPTION OF THE INVENTION

All percentages and ratios used herein are by weight of the total composition and all measurements are made at 25° C., unless otherwise designated.

The term "PHA" as used herein means polyhydroxyalkanoate.

As stated above, the invention provides processes for extracting polyhydroxyalkanoate from a biomass, comprising admixing the biomass with an organic solvent for from 1 second to 15 minutes at a first temperature of from 5° C. below the melting point of the polyhydroxyalkanoate to 10° C. above the melting point of the polyhydroxyalkanoate and at a pressure of from 1 bar to 10 bar to provide a composition comprising the organic solvent and polyhydroxyalkanoate.

I. Admixing the Biomass With an Organic Solvent a) Biomass Containing PHA

Polyhydroxyalkanoates can be extracted using the processes of the present invention from sources including, but not limited to, single-celled organisms, such as bacteria or fungi, and higher organisms, such as plants. These sources, together with the PHAs that are biosynthesized, are collectively referred to herein as "biomass". While biomass can comprise wild-type organisms, they also can comprise genetically engineered species specifically designed for the production of particular PHAs of interest. Methods for making such genetically engineered organisms are well known to those skilled in the art.

The biomass can be substantially dry. As used herein, "substantially dry" means containing less than 5% water. Substantially dry biomass can be obtained using processes including, but not limited to, spray, rotary drum, or freeze drying, before the extraction process is initiated. In one embodiment, a substantially dry biomass contains less than 2% water; in another embodiment, less than 1% water, alternatively, the biomass contains no detectable level of water.

Plants useful as biomass organisms include any genetically engineered plant capable of producing PHAs. Such plants include agricultural crops such as cereal grains, oilseeds and tuber plants; other plants include avocado, barley, beet, broad bean, buckwheat, carrot, coconut, copra, corn (maize), cottonseed, gourd, lentil, lima bean, millet, mung bean, oat, oilpalm, pea, peanut, potato, pumpkin, rapeseed (e.g., canola), rice, sorghum, soybean, sugarbeet, sugar cane, sunflower, sweet potato, tobacco, wheat, and yam. Such genetically altered fruit-bearing plants useful in the process of the present invention include, but are not limited to, apple, apricot, banana, cantaloupe, cherry, grape, kumquat, tangerine, tomato, and watermelon. The plants can be genetically engineered to produce PHAs according to the methods disclosed in Poirier, Y., D. E. Dennis, K. Klomparens and C. Somerville, "Polyhydroxybutyrate, a biodegradable thermoplastic, produced in transgenic plants'" SCI- ENCE, Vol. 256, pp. 520–523 (1992); and/or U.S. Pat. No. 5,650,555 to Michigan State University, issued Jul. 22, 1997. In one embodiment, the plants are soybean, potato, corn, or coconut plants that are genetically engineered to produce PHAs; in another embodiment, the plant is soybean.

Bacteria that are useful in the present invention include any genetically engineered bacteria that can produce PHAs, as well as bacteria which naturally produce PHAs. Examples of such bacteria include those disclosed in NOVEL BIODEGRADABLE MICROBIAL POLYMERS, E. A. Dawes, ed., NATO ASI Series, Series E: Applied Sciences—Vol. 186, Kluwer Academic Publishers (1990); U.S. Pat. No. 5,292,860 to Kanegafuchi Kagaku Kogyo Kabushiki Kaisha, issued Mar. 8, 1994. In one embodiment, the bacterium is *Alcaligenes eutrophus, Escherichia coli, Protomonas extorquens, Methylobacterium extorquens, Pseudomonas putida, Pseudomonas resinovorans, Pseudomonas oleovorans, Pseudomonas aeruginosa, Pseudomonas syringae, Pseudomonas fluorescens, Sphaerotilus natans, Agrobacterium, Rhodobacter sphaeroides, Actinobacillus*, or *Azotobacter vinelandii*.

In one embodiment, the biomass contains a quantity of PHA that is sufficient to make the extraction process described in the present invention economically desirable. In another embodiment, the amount of PHA in the biomass is at least about 20% of the total dry weight of the biomass; in another embodiment, at least 50%; in another embodiment, at least about 60%. In one embodiment, the initial amount of PHA in the biomass is from about 25% to about 90% of the total dry weight of the biomass.

b) Structurally Flexible PHAs:

One or more types of PHAs can be extracted from the biomass.

In one embodiment, the PHAs of the present invention are those referred to herein as "structurally flexible" PHAs, in that the physical disruption caused by the relatively high co-monomer content or particular pendant group chain length, make them generally more ductile and more difficult to crystallize than PHAs that are characterized by lower co-monomer content and shorter pendant groups. Examples of structurally flexible PHAs are disclosed in U.S. Pat. Nos. 5,602,227, RE 36,548, and 6,077,931; and U.S. Pat. Nos. 6,043,063 and 6,087,471.

In one embodiment, the PHAs that are useful in the present invention have a first repeat unit of the structure:

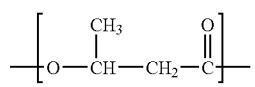

and a second repeat unit having the structure:

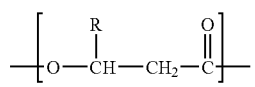

wherein each R is independently a $C_3$ to $C_{19}$ alkylene group; and wherein the PHA has from about 75 mol % to about 99 mol % of the first repeat unit, and from about 1 mol % to about 25 mol % of the second repeat unit.

The first and second repeat units can be randomly repeating units. PHAs of the present invention include, for example, random copolymers and block copolymers.

The PHAs of the present methods can have a melt temperature ("Tm") of from about 80° C. to about 160° C.

In one embodiment, the second repeat unit is 3-hydroxyhexanoate. In another embodiment, the PHA is a hydroxybutyrate-hydroxyhexanote copolymer.

In another embodiment, the PHA is a poly(3-hydroxyalkanoate). In one embodiment, the poly(3-hydroxyalkanoate) is a poly(D-3-hydroxyalkanoate).

In another embodiment, the PHA is a poly(3-hydroxybutyrate)-poly(4-hydroxybutyrate).

The present invention is applicable to PHAs covering a wide range of molecular weights. In one embodiment, the polyhydroxyalkanoate has a molecular weight of from about 100,000 to about 1,500,000. In another embodiment, the PHA has a molecular weight of from about 300,000 to about 800,000.

c) Organic Solvent:

The biomass containing the PHA is admixed with an organic solvent.

In one embodiment, the organic solvent is an alcohol, a $C_3$–$C_7$ ketone, toluene, ethyl acetate, tetrahydrofuran, acetonitrile, glyme, methyl ester, sulfolane, DMSO, or a combination thereof. Alcohols useful herein include linear or branched alcohols. Exemplary alcohols include methanol, ethanol, n-propanol, isopropanol, n-butanol, isobutanol, isopentanol, sec-pentanol, t-pentanol, or a combination thereof. $C_3$–$C_7$ ketones useful herein include acetone, methyl ethyl ketone, diethylketone, cyclohexanone or a combination thereof.

In one embodiment, the organic solvent is substantially anhydrous. As used herein, the term "substantially anhydrous" means comprising less than about 1% water; in another embodiment, comprising less than about 0.5% water; in another embodiment, comprising less than about 0.1% water.

The present methods can be performed using an organic solvent to PHA ratio that is typically lower than that of other extraction systems known in the art. In one embodiment, the ratio of organic solvent to polyhydroxyalkanoate is from about 5 parts to about 100 parts organic solvent to about one part polyhydroxyalkanoate by weight. In another embodiment, the ratio of organic solvent to polyhydroxyalkanoate is from about 5 to about 30 parts organic solvent to about one part polyhydroxyalkanoate by weight. In another embodiment, the ratio of organic solvent to polyhydroxyalkanoate is from about 10 parts to about 20 parts organic solvent to about one part polyhydroxyalkanoate by weight. In another embodiment, the ratio of organic solvent to polydroxyalkanoate is from about 15 parts organic solvent to about one part polyhydroxyalkanoate by weight. In one embodiment, the biomass comprises from about 30% to about 90% of PHA by weight, alternatively the biomass comprises about 60% by weight.

In one embodiment, the biomass comprises less than about 8% water; in another embodiment, less than about 5% water, in another embodiment, less than about 2% water, alternatively, the biomass comprises no measurable quantity of water.

One of skill in the art will recognize that the selection of organic solvent can be based on a number of factors, including enhancing PHA solubility at moderate temperatures and/or pressures, enhancing the precipitation or separation of PHA at lower temperatures, the ability of the organic solvent to serve as a washing agent, the molecular weight stability of the PHA to be extracted, compatibility of the organic solvent with the biomass type (either dry or wet), the volume of the organic solvent required, and the cost of the organic solvent.

d) Admixing Time, Temperature, and Pressure

The biomass is admixed with an organic solvent for from about 1 second to about 15 minutes at a first temperature that is from about 5° C. below the melting point of the polyhydroxyalkanoate to about 10° C. above the melting point of the PHA and a pressure of 1 bar to about 10 bar to provide a composition comprising the organic solvent and polyhydroxyalkanoate.

As used herein, the term "melting point of the PHA" means a temperature at which at least about 70% of the PHA is melted; in another embodiment, at least 80% of the PHA is melted; in one embodiment, at least 90% of the PHA is melted; in another embodiment, at least 95% of the PHA is melted; in another embodiment, at least 98% of the PHA is melted.

In one embodiment, the admixing occurs for from about 1 second to about 10 minutes. In another embodiment, the admixing occurs for from about 30 seconds to about 10 minutes. In one embodiment, the admixing occurs for from about 5 to about 15 minutes. In one embodiment, the admixing occurs for from about 5 to about 10 minutes. In another embodiment, the admixing occurs for about 10 minutes.

In one embodiment, the admixing occurs at a first temperature that is about 2° C. to about 10° C. above the melting point of the PHA. In another embodiment, the admixing occurs at a first temperature that is about 2° C. to about 5° C. above the melting point of the PHA.

In one embodiment, the admixing occurs at a first temperature that is about 5° C. above the melting point of the PHA for about 10 minutes to about 15 minutes.

In one embodiment, the admixing occurs at a pressure that is from about 1 bar to about 6 bar. One of skill in the art will recognize that the pressure will be a function of the first temperature and organic solvent. One of skill in the art will further appreciate that depending on the organic solvent used, the pressure can be adjusted to provide the desired temperature even where the temperature is above the ambient boiling point of the desired solvent. As such, the pressure of the system can depend on the solvent. For example, for a high boiling solvent such as DMSO, the pressure required to reach the first temperature can be about 1 bar. For a lower boiling solvent such as acetone, the pressure required to reach the first temperature can be about 6 bar.

Applicants believe that the methods herein can provide a number of advantages over extraction methods that are known in the art. For a given solvent, the solubility of PHA in the organic solvent can be enhanced by melting the PHA by heating above about the melting point of the PHA. The solubility of PHA in the organic solvent can also be enhanced by breaking the crystallinity of the PHA by heating to about 5° C. below the melting point of the PHA. The present invention can be performed using less solvent than that used in prior art extraction processes. The present invention is also advantageous in that the solvent-PHA residence time can be shorter than that of prior-art extraction processes. The present invention can provide PHA in its molten form, which makes the overall extraction process more feasible, and can allow loading higher amounts of PHA into the organic solvent in a lower time.

II. Maintaining the Organic Solvent Within a Second Temperature Range

In one embodiment, the processes further comprise maintaining the composition within a second temperature range, which is from about ambient temperature to about the melting point of the polyhydroxyalkanoate, subsequent to admixing at the first temperature.

In one embodiment, the extraction further comprises admixing the composition with additional organic solvent, for example prior to the maintaining step. One of skill in the art will recognize that the additional organic solvent can be the same as or different than the organic solvent with which the biomass is admixed in the admixing step. The additional organic solvent can optionally be preheated prior to admixing with the composition. In one embodiment, the organic solvent is preheated at a temperature within the second temperature range.

In one embodiment, the maintaining occurs for from about 5 to about 120 minutes. In another embodiment, the maintaining occurs for about 60 minutes.

In one embodiment, the second temperature range is from about 80° C. to about 130° C. In another embodiment, the second temperature range is from about 80° C. to about 120° C. In one embodiment, the second temperature range is from about 80° C. to about 100° C.

In another embodiment, the maintaining occurs for from about 5 to about 120 minutes at a temperature of from about 80° C. to about 130° C.

In one embodiment, the processes further comprises mixing during maintaining the organic solvent at the second temperature. Mixing can be performed by any methods useful for mixing compositions. For example, the mixing can be performed using a propeller, a turbine, a screw conveyor, or a combination thereof. In one embodiment, the mixing can be performed by using a plug flow concept with a screw conveyor.

In one embodiment, subsequent to admixing, the process further comprises maintaining the biomass with an organic solvent for from about 5 to about 120 minutes at a second temperature of from about 80° C. to about 130° C.; separating the polyhydroxyalkanoate from the organic solvent; and isolating the polyhydroxyalkanoate.

III. Separation of PHA from Organic Solvent

In one embodiment, the processes further comprise separating the polyhydroxyalkanoate from the organic solvent subsequent to maintaining the organic solvent within the second temperature range.

In one embodiment, the separating occurs at a third temperature, which is from about 50° C. to about 90° C. In another embodiment, the separating occurs at a third temperature, which is from about 70° C. to about 90° C. In another embodiment, the separating occurs at a third temperature, which is from about 50° C. to about 70° C.

Separating the PHA from the organic solvent can comprise filtration, precipitation, centrifugation, or a combination thereof. In one embodiment, the filtration is performed at a temperature of at least about 40° C. to about 90° C. In another embodiment, the filtration is performed at a temperature of from about 45° C. to about 70° C. In one embodiment, the centrifugation is performed at a temperature of from about 40° C. to about 90° C.

IV. Precipitation

In one embodiment, the separating comprises precipitating the PHA from the organic solvent to form precipitated polyhydroxyalkanoate. In one embodiment, the precipitating comprises cooling, flashing, or a combination thereof.

In one embodiment, the precipitating is achieved by admixing the organic solvent with water or an organic solvent in which PHA is substantially insoluble at a temperature below about 50° C. As used herein, the term "substantially insoluble" means that no more than about 1% of PHA is soluble by weight; in another embodiment, no more than 0.5% PHA is soluble by weight; in another embodiment, no more than 0.1% PHA is soluble by weight. In another embodiment, the precipitating is achieved by admixing the water or the organic solvent in which PHA is substantially insoluble at a temperature below about 50° C. to the organic solvent. In one embodiment, the admixing in this regard occurs using propellers, turbines, homogenizers, layers of water coated sheets, moving belts, high shear mixers, and combinations thereof. In one embodiment, a tip speed can be selected to obtain the desired product morphology.

In one embodiment, the precipitating comprises cooling the organic solvent to a temperature of from about 20° C. to about 45° C.

V. Isolation

In one embodiment, the process further comprises isolating the precipitated PHA from the organic solvent. In one embodiment, filtration can be used to recover the precipitated PHA.

In addition to filtration, the isolated PHA can be squeezed and/or placed under pressure in order to remove any remaining organic solvent.

In addition to filtration and/or other recovery methods, the isolated PHA can then be washed with a solvent selected from $C_3$–$C_7$ ketones such as acetone, methyl ethyl ketone, alcohols such as ethanol, methanol, hydrocarbons such as hexane, heptane, or a mixture thereof.

VI. Drying

In one embodiment, the isolated PHA can be dried using well-known methods to remove any remaining organic solvent.

VI. Recycling of Solvent

After the step of isolating the PHA, in one embodiment, the organic solvent can be recovered and recycled and/or re-used by well-known methods.

VII. Other Process Parameters

In one embodiment, depending on the type of morphology (flake, fiber, powder, film) desired in the precipitated PHA, process parameters can be altered to obtain such morphologies. For example, the method of precipitation may be used as a tool to enable the neat polymers morphology (flake, fiber, powder, film) and enhance the purity of the product.

One of skill will recognize that the optimal range of unit operating conditions or individual devices could vary according to the type of raw biomass.

Therefore, the following examples further describe and demonstrate certain embodiments within the scope of the present invention. The examples are given solely for the purpose of illustration, and are not to be construed as limitations of the present invention since many variations of the present invention are possible without departing from its spirit and scope.

EXAMPLES

Example 1

Melting and Dissolving PHA Using PHA Extraction Solvent

To 100 kg of dried biomass containing approximately 60% PHA (polyhydroxybutyrate and hydroxyhexanoate copolymer having about 6 mole % of hydroxyhexanoate), is added approximately 200 kg of toluene at about 150° C., which is about 5° C. above the melting temperature of the polymer. The temperature of the mixture is maintained at about 150° C. for 15 minutes in a pressure reactor. 800 kg of toluene at 70° C. is then added, and the temperature of the resultant mixture is maintained at between 85° C. and 90° C. for 60 minutes. The PHA-toluene solution is then filtered at 80–90° C. The filtrate is cooled to 50° C. 1000 kg of hexane is added to the filtrate under mild or no agitation, precipitating the PHA. The PHA is filtered from the solvents and dried using a rotary drier under vacuum at 60° C. About 55 kg of dried PHA is the expected yield. Solvents are recovered and recycled.

Example 2

Melting and Dissolving PHA Using PHA Extraction Solvent

To 100 kg of dried biomass containing approximately 60% PHA (polyhydroxybutyrate and hydroxyhexanoate copolymer with about 6 mole % of hydroxyhexanoate), is added approximately 200 kg of toluene at 150° C. The temperature is maintained at 150° C. for 10 minutes. The material is then cooled to 120° C. and about 800 kg of toluene is added at 70° C. The temperature is then maintained at 85° C. for 60 minutes. The solution is filtered to remove spent biomass at a temperature of about 80° C. The filtrate is cooled to 45° C. and is diluted with 1000 kg of heptane, precipitating the PHA. The PHA is washed with 200 kg of ethanol. The PHA is filtered and dried at 90° C. About 55 kg of dry PHA is expected yield.

Example 3

Melting and Dissolving PHA Using PHA Extraction Solvent

To 100 kg of dried biomass containing approximately 60% PHA (polyhydroxybutyrate and hydroxyhexanoate copolymer having about 9 mole % of hydroxyhexanoate), is added approximately 200 kg of toluene at about 140° C., which is about 5° C. above the melting temperature of the polymer. The temperature of the mixture is maintained at about 140° C. for 10 minutes in a pressure reactor. 800 kg of toluene at 70° C. is then added, and the temperature of the resultant mixture is maintained at between 85° C. and 90° C. for 60 minutes. The PHA-toluene solution is then filtered at 80–90° C. The filtrate is cooled to 50° C. 1000 kg of hexane is added to the filtrate under mild or no agitation, precipitating the PHA. The PHA is filtered from the solvents and dried using a rotary drier under vacuum at 60° C. About 55 kg of dried PHA is the expected yield. Solvents are recovered and recycled.

Example 4

Melting and Dissolving PHA Using PHA Extraction Solvent

To 100 kg of dried biomass containing approximately 60% PHA (polyhydroxybutyrate and hydroxyhexanoate copolymer having about 9 mole % of hydroxyhexanoate), is added approximately 200 kg of acetone at about 140° C., which is about 5° C. above the melting temperature of the polymer. The temperature of the mixture is maintained at about 140° C. for 15 minutes in a pressure reactor. 800 kg of acetone at 70° C. is then added, and the temperature of the resultant mixture is maintained at between 85° C. and 90° C. for 60 minutes. The PHA-toluene solution is then filtered at 80–90° C. The filtrate is cooled to 50° C. 1000 kg of water is added to the filtrate under mild or no agitation, precipitating the PHA. The PHA is filtered from the solvents and dried using a rotary drier under vacuum at 60° C. About 55 kg of dried PHA is the expected yield. Solvents are recovered and recycled.

Throughout this application, various publications are referenced. The disclosures of these publications in their entireties are hereby incorporated by reference into this application in order to more fully describe the state of the art as known to those skilled therein as of the date of the invention described and claimed herein.

The disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for extracting polyhydroxyalkanoate from a biomass, comprising:
   admixing the biomass with an organic solvent for from about 1 second to about 15 minutes at a temperature of from about 5° C. below the melting point of the polyhydroxyalkanoate to about 10° C. above the melting point of the polyhydroxyalkanoate and at a pressure of from about 1 bar to about 10 bar to provide a composition comprising the organic solvent and polyhydroxyalkanoate.

2. The process of claim 1, further comprising maintaining the composition within a temperature range, which is from ambient temperature to the melting point of the polyhydroxyalkanoate.

3. The process of claim 2, further comprising admixing the composition with additional organic solvent.

4. The process of claim 2, wherein the maintaining occurs for from 5 to 120 minutes.

5. The process of claim 2, wherein the temperature range is from 80° C. to 130° C.

6. The process of claim 2, further comprising separating the polyhydroxyalkanoate from the organic solvent subsequent to the maintaining.

7. The process of claim 6, wherein the separating comprises precipitating the polyhydroxyalkanoate from the organic solvent to form precipitated polyhydroxyalkanoate.

8. The process of claim 7, further comprising isolating the precipitated polyhydroxyalkanoate.

9. The process of claim 1, wherein the organic solvent is an alcohol, a $C_3$–$C_7$ ketone, or a combination thereof.

10. The process of claim 1, wherein the organic solvent is methanol, ethanol, propanol, butanol, pentanol, acetone, methyl ethyl ketone, or a combination thereof.

11. The process of claim 1, wherein the solvent is toluene, ethyl acetate, tetrahydrofuran, acetonitrile, glyme, methyl ester, sulfolane, DMSO, or a combination thereof.

12. The process of claim 1, wherein the organic solvent is substantially anhydrous.

13. The process of claim 1, wherein the ratio of organic solvent to polyhydroxyalkanoate is from 5 to 100 parts organic solvent to one part polyhydroxyalkanoate by weight.

14. The process of claim 1, wherein the ratio of organic solvent to polyhydroxyalkanoate is from 15 parts organic solvent to one part polyhydroxyalkanoate by weight.

15. The process of claim 1, wherein the first temperature is from 2° C. to 5° C. above the melting point of the polyhydroxyalkanoate.

16. The process of claim 1, wherein the admixing occurs for from 5 to 15 minutes.

17. The process of claim 2, wherein the temperature range is from 80° C. to 100° C.

18. The process of claim 1, wherein the process is a continuous process.

19. The process of claim 2, further comprising mixing the organic solvent while maintaining it within the temperature range.

20. The process of claim 19, where the mixing is achieved using a propeller, turbine, screw conveyor, or a combination thereof.

21. The process of claim 2, wherein the maintaining occurs for 60 minutes.

22. The process of claim 6, wherein the separating comprises filtering, centrifuging, or a combination thereof.

23. The process of claim 6, wherein the separating occurs at a temperature, which is from 50° C. to 70° C.

24. The process of claim 7, wherein the precipitating comprises cooling, flashing, or a combination thereof.

25. The process of claim 7, wherein the precipitating is achieved by admixing the organic solvent with water or an organic solvent in which polyhydroxyalkanoate is substantially insoluble at a temperature below 50° C.

26. The process of claim 25, wherein the admixing occurs using a propeller, turbine, high shear, layers of water coated sheets, moving belts, or a combination thereof.

27. The process of claim 1, wherein the polyhydroxybutyrate is a hydroxybutyrate-hydroxyhexanoate copolymer with a molecular weight of from 100,000 to 1,500,000.

28. The process of claim 1, further comprising:
   a) maintaining the organic solvent for from 5 to 120 minutes at a temperature of from 80° C. to 100° C.;
   b) separating the polyhydroxyalkanoate from the organic solvent; and
   c) isolating the polyhydroxyalkanoate;

wherein the polyhydroxyalkanoate has a first repeat unit having the structure:

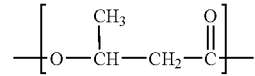

and a second repeat unit having the structure:

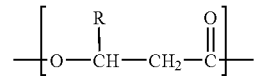

wherein each R is independently a $C_3$ to $C_{19}$ alkylene group; and wherein the polyhydroxyalkanoate has from 75 mol % to 99 mol % of the first repeat unit and from 1 mol % to 25 mol % of the second repeat unit.

29. The process of claim 1 or claim 28, wherein the polyhydroxyalkanoate is a poly(3-hydroxyalkanoate).

* * * * *